United States Patent [19]

Farr

[11] Patent Number: 4,986,807
[45] Date of Patent: Jan. 22, 1991

[54] ATHERECTOMY CUTTER WITH RADIALLY PROJECTING BLADE

[75] Inventor: Andrew F. Farr, Spring Valley, Calif.

[73] Assignee: InterVentional Technologies, Inc., San Diego, Calif.

[21] Appl. No.: 299,147

[22] Filed: Jan. 23, 1989

[51] Int. Cl.[5] .............................................. A61B 17/32
[52] U.S. Cl. ........................................ 604/22; 606/159
[58] Field of Search ............... 606/106, 159, 170, 171; 604/27, 35, 49, 52, 53, 22

[56] References Cited

U.S. PATENT DOCUMENTS

| | | | |
|---|---|---|---|
| 2,729,210 | 1/1956 | Spencer | 128/2 |
| 2,749,909 | 6/1956 | Ullery et al. | 128/2 |
| 3,512,519 | 5/1970 | Hall | 128/2 |
| 3,605,721 | 9/1971 | Hallac | 128/2 |
| 3,815,604 | 6/1974 | O'Malley et al. | 128/305 |
| 3,990,453 | 11/1976 | Douvas et al. | 128/305 |
| 4,111,207 | 9/1978 | Seiler, Jr. | 606/171 |
| 4,273,128 | 6/1981 | Lary | 128/305 |
| 4,320,762 | 3/1986 | Bentov | 128/343 |
| 4,441,509 | 4/1986 | Kotsifas et al. | 128/757 |
| 4,589,412 | 5/1986 | Kensey | 128/305 |
| 4,598,710 | 7/1986 | Kleinberg et al. | 128/318 |
| 4,603,694 | 8/1986 | Wheeler | 606/171 |
| 4,610,662 | 9/1986 | Weikl et al. | 604/53 |
| 4,627,436 | 12/1986 | Leckrone | 128/303 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell et al. | 128/305 |
| 4,771,774 | 9/1988 | Simpson et al. | 606/171 |

OTHER PUBLICATIONS

Coronary Artery Incision and Dilation, B. G. Lary, M.D., Archives of Surgery, Dec. 1980, vol. 115, pp. 1478-1480.
Method for Increasing the Diameter of Long Segments of the Coronary Artery, B. G. Lary, M.D., The American Surgeon, Jan. 1966, vol. 32, No. 1, pp. 33-35.
A Method for Creating a Coronary-Myocardial Artery, B. G. Lary, M.D., et al., Surgery, St. Louis, vol. 59, No. 6, pp. 1061-1064.

Primary Examiner—Robert A. Hafer
Assistant Examiner—Lynda M. Cofsky
Attorney, Agent, or Firm—Neil K. Nydegger

[57] ABSTRACT

An atherectomy device for cutting obstructive tissue from the lumen of a body vessel comprises a rotatable cutter having a blade. A hollow, generally cylindrical housing defines a central longitudinal axis and has a side opening. The cutter is mounted in the housing for rotation about an axis that is substantially parallel to the longitudinal axis of the housing. During rotation of the cutter, the blade cyclically projects from the side opening to cut obstructive tissue from the lumen.

11 Claims, 2 Drawing Sheets

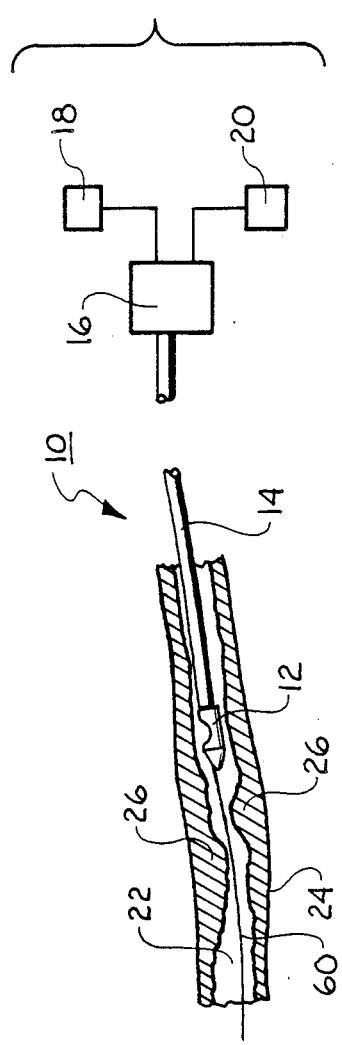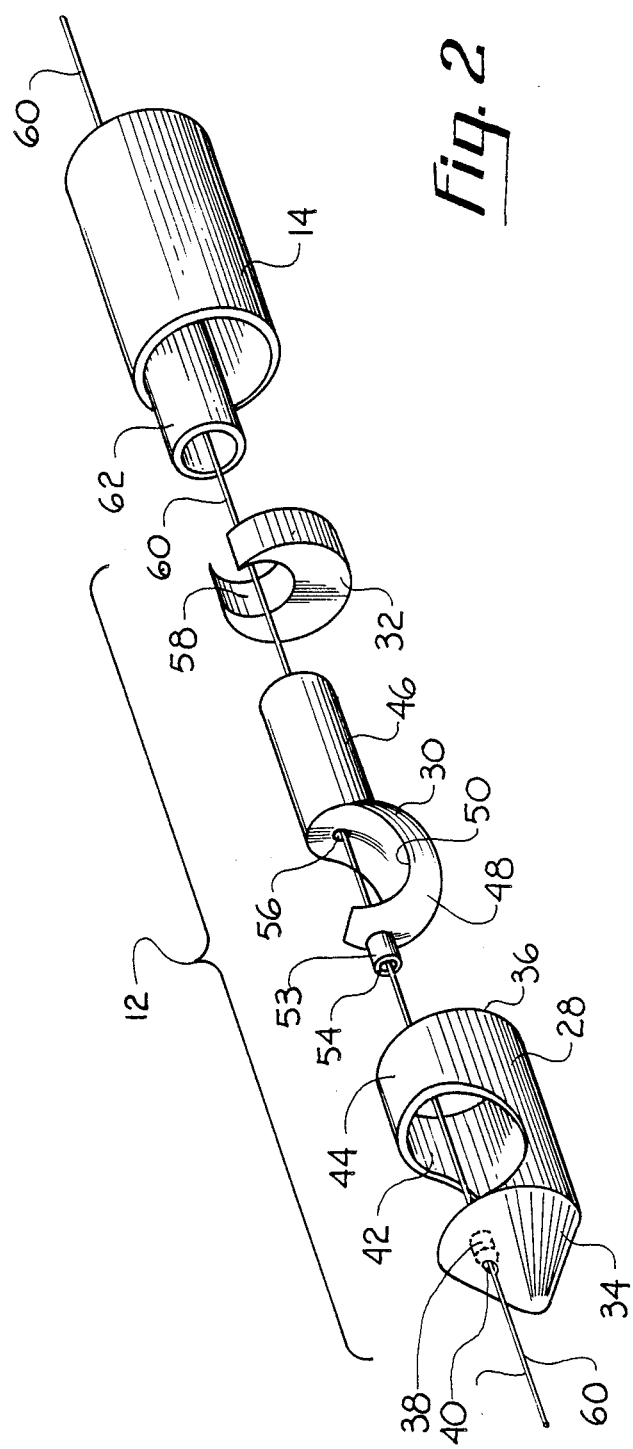

ATHERECTOMY CUTTER WITH RADIALLY PROJECTING BLADE

FIELD OF THE INVENTION

This invention relates generally to cutting devices. More specifically, the present invention relates to devices which are useful for cutting and removing obstructive tissue from the lumen of a body vessel. This invention is particularly, but not exclusively, suited for use as a cutting device in an atherectomy procedure where the opening to be cut through the obstructive tissue needs to be larger than the minimum cross-sectional dimensions of the cutting device.

BACKGROUND OF THE INVENTION

In recent years, various means and procedures have been developed to clear or open occluded arteries and other body vessels in order to restore the necessary circulation of fluids such as blood, through the body. In many situations, such intravessel procedures are preferable to the so-called "bypass" operations because such procedures can be relatively quickly performed and do not require an incision into the chest cavity or some other part of the body. Consequently, various procedures and several different devices for performing these procedures have been developed.

There are generally three ways to eliminate or ameliorate the difficulties caused by an occlusion in a body vessel. First, it may be possible to dissolve the obstructive tissue causing the occlusion by the ingestion or injection of properly selected medicaments. Such treatment, however, may be ineffective due to an excessive time for response, or undesirable due to adverse side effects. Second, well known angioplasty procedures utilizing a balloon catheter may be used to attempt to flatten the obstructive tissue against the vessel wall. With the angioplasty procedures, however, the obstructive tissue causing the occlusion remains in situ after the procedure is performed. Thus, the problem may be compromised but it is not eliminated and there remains the real probability there will be a restenosis. Third, atherectomy related procedures may be performed.

In any atherectomy procedure, the obstructive tissue causing the occlusion in the vessel (or at least a part of this obstructive tissue) is cut or clipped from the lumen of the vessel. As should be readily apparent, the instruments used for this purpose require specifically designed cutting devices. Further, the devices which are used for controlling the position of the cutting device in the lumen require special fabrication and design considerations. Specifically, both the cutting device itself and whatever control elements are inserted into the vessel with the cutting device must be miniaturized.

Several atherectomy related devices have been previously disclosed. Exemplary of such devices is U.S. Pat. No. 4,754,755 to Husted which discloses a catheter with a cylindrical rotary blade that is used to clear arterial obstructions. As another example of an atherectomy device, U.S. Pat. No. 4,732,154 to Shiber discloses a rotary catheter system for this same purpose. For each of the devices disclosed in these references, however, the effective cutting area of the blade of the device is limited. This is so because, in these typical devices, the cutting action of the rotating blade is not capable of extending beyond the periphery of the tubular structure which is used to introduce the blade into the vessel. Consequently, the effective cutting radius of the blade once inside the vessel is limited by the size of the opening used for an entry site. It usually happens, however, that the cross-sectional area of the vessel lumen at the obstruction location is greater than the maximum permissible size of the opening for an entry site. Thus, there is a need for a cutter which has an extended cutting capacity. Accordingly, the present invention recognizes the need for an atherectomy cutter whose effective cutting action radius can be extended, once it is positioned within the lumen of a body vessel, to increase the cutting effectiveness of the device.

It is thus an object of the present invention to provide a cutter for an atherectomy device which can be expanded once it is inside the lumen of a body vessel. Another object of the present invention is to provide an atherectomy device which can be operatively positioned within the lumen as required to excise obstructive tissue from inside the lumen of a body vessel. Still another object of the present invention is to provide an atherectomy device which can be effectively controlled during the cutting of obstructive tissue from the inside of a body vessel. Yet another object of the present invention is to provide an atherectomy device which is easy to use, relatively easy to manufacture and comparatively cost effective.

SUMMARY OF THE INVENTION

A preferred embodiment of the novel atherectomy device includes a hollow, generally cylindrical housing which has an open end, a closed end, and an opening through its side wall. A cutter formed with a curved blade is mounted in the housing for rotation about an axis which is substantially parallel to the longitudinal axis of the housing. An aligned passageway is formed through the cutter and the housing, and a hollow torque tube is fixedly attached to the cutter in fluid communication with the passageway. The torque tube can be driven to rotate the cutter and a guide wire can be inserted through the torque tube and the passageway. Thus, with the guide wire inserted into the lumen of a body vessel, the cutter and housing combination can be advanced along the guide wire and into contact with obstructive tissue in the lumen. While being advanced to the obstructive tissue site, the cutter may be positioned so it is wholly contained within and does not project from the housing. Once at the site, the cutter is rotated and its blade cyclically projects through the opening in the side of the housing to cut the obstructive tissue in the lumen.

A sheath, surrounding the torque tube, is attached to the housing to stabilize the combination and facilitate insertion of the combination into the lumen of the body vessel. Also, a suction device may be operatively connected to the torque tube to remove cuttings from the obstructive tissue through the passageway and torque tube.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a cross-sectional view of a body vessel with the atherectomy device of the present invention shown positioned against obstructive tissue and a connected schematic diagram of the control elements;

FIG. 2 is an exploded perspective view of the atherectomy device;

DESCRIPTION OF THE PREFERRED EMBODIMENT

Figure 3C:
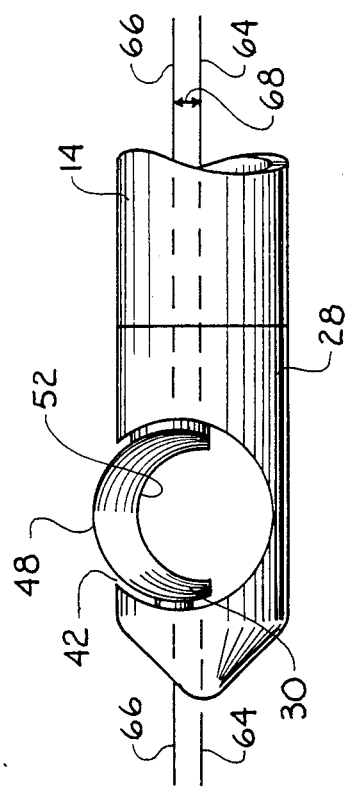
FIG. 3A, 3B and 3C are side elevational views of the atherectomy device with its cutter in sequential positions.

Referring intially to FIG. 1, the atherectomy device of the present invention, generally designated 10, is seen in its operational environment. As shown, device 10 comprises a tip 12 connected at the distal end of a sheath 14. Connected to the proximal end of sheath 14 is a control unit 16 which includes a suction pump 18 and a driver assembly 20. To function in its intended operative environment, the tip 12 of atherectomy device 10 is inserted into the lumen 22 of a body vessel 24, over a guide wire 60 by a procedure well known in the pertinent art, and urged into contact with obstructive tissue 26. Device 10 can then be operated to cut and remove obstructive tissue 26 from lumen 22 as will be more fully explained below.

The component elements of tip 12 will be best appreciated by reference to FIG. 2 in which it can be seen that tip 12 collectively comprises a housing 28, a cutter 30 and a bushing 32 More specifically, housing 28 is generally cylindrical in shape and is formed with a closed end 34 and an open end 36. The closed end 34 is smooth and is preferably rounded to facilitate insertion of tip 12 through lumen 22 of vessel 24. Closed end 34 is also formed with a seat 38 (shown in phantom) and a hole 40 which extends from seat 38 through closed end 34. Housing 28 is also formed with an opening 42 in its side wall 44. As shown, opening 42 is on the periphery of housing 28 and is formed to accommodate a spherical shape having a center which is radially oriented relative to the central longitudinal axis defined by the cylindrical-shaped housing 28.

Cutter 30 is formed with a shaft 46 and a cutting portion 48. More specifically, cutting portion 48 is rounded and extends from shaft 46 to define a curved blade 50 on one side of the cutting portion 48 and another curved blade 52 on the opposite side of cutting portion 48. Additionally, cutter 30 includes an extension 53 which is formed with a hole 54 that extends through extension 53 along its longitudinal axis. A passageway 56 is formed along the longitudinal axis of, and is coaxially aligned with, hole 54. Further, FIG. 2 shows that the bushing 32 is formed with a channel 58 which is dimensioned to receive shaft 46 of cutter 30.

In the assembly of tip 12, cutter 30 is positioned in housing 28 with its extension 53 inserted into seat 38. The bushing 32 is then disposed in the open end 36 of housing 28 to cradle shaft 46 in channel 58. Importantly, as so assembled, the axis of rotation for cutter 30 is set off from, and substantially parallel to, the central longitudinal axis of the cylindrical shaped housing 28. Also, with this assembly, hole 40 in housing 28, hole 54 in extension 53 and passageway 56 in shaft 46 are coaxially aligned with each other to slidingly receive a guide wire 60. Thus, the assembled tip 12 can be moved along guide wire 60 to position tip 12 at any desired location on guide wire 60. Independently from this sliding movement of tip 12 along guide wire 60, cutter 30 can be rotated within housing 28. Specifically, a torque tube 62 is fixedly attached to shaft 46 by any means well known in the pertinent art, such as by gluing or solvent bonding, for the transmission of power from driver assembly 20 to cutter 30 for the rotation of cutter 30. As perhaps best seen in FIG. 3A, sheath 14 is fixedly attached to housing 28, by any means well known in the pertinent art, and positioned in surrounding relationship with torque tube 62. With this attachment, sheath 14 provides stability for tip 12 and protects vessel 24 from the rotational action imparted to torque tube 62 by driver assembly 20.

Figure 3A:
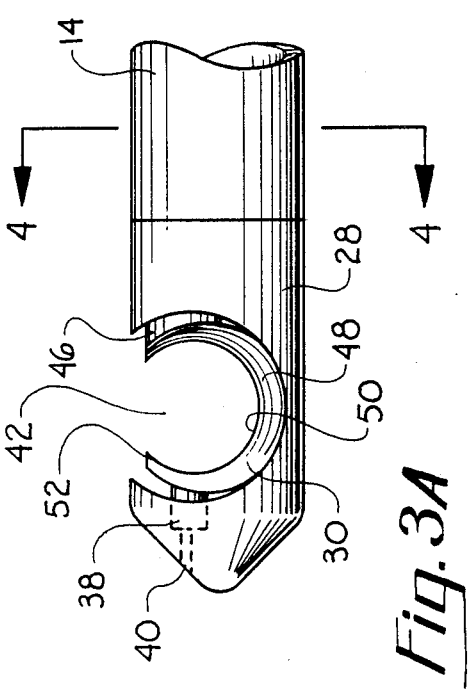
Figure 3B:
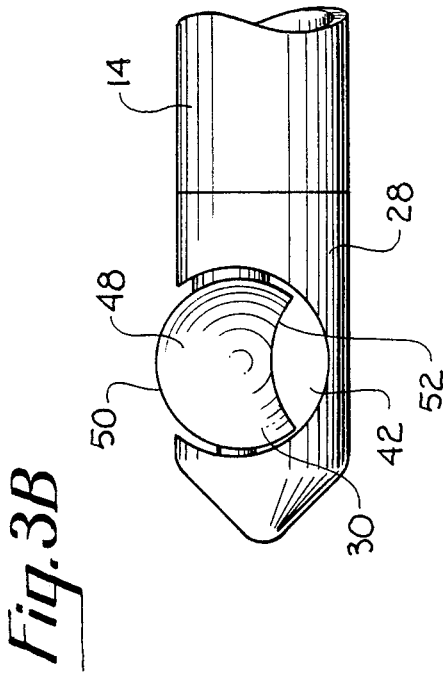

The rotational action of cutter 30 will be best appreciated by cross referencing FIGS. 3A, 3B and 3C. In FIG. 3A, cutter 30 is shown in a withdrawn position wherein cutting portion 48 is contained within housing 28. Importantly, when tip 12 is in this configuration, the effective cross-sectional area at any point along the length of device 10 will be no greater than the largest cross-sectional area of sheath 14. This facilitates insertion of the device 10 into and through vessel 24 of the patient (not shown). It will be seen, however, that as cutter 30 is rotated in housing 28 to expose blade 50, the blade 50 projects from housing 28 through opening 42. Specifically, FIG. 3B shows cutting portion 48 in its position after cutter 30 has been rotated approximately 135° from its position shown in FIG. 3A. Further, FIG. 3C shows the position of cutter 30 after a rotation of 180° from its position shown in FIG. 3A. As seen in FIGS. 3B and 3C, this sequence causes blade 50 to project beyond the periphery of housing 28. Consequently, a larger cutting area can be realized than is possible without such projection. It is to be appreciated that cutter 30 may be rotated either clockwise or counterclockwise. Thus, depending on the direction of rotation, blade 50 or blade 52 may do the actual cutting.

Figure 4:
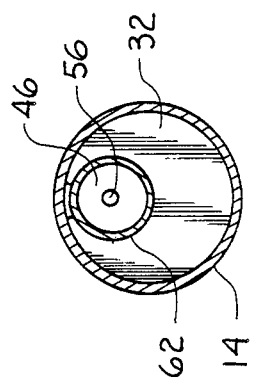
FIG. 4 is a cross—sectional view of the atherectomy device as seen along the line 4—4 in FIG. 3A.

The generating of the cutting action of cutter 30 will perhaps be best appreciated by reference to FIG. 3C wherein the axis 64 represents the central longitudinal axis of housing 28. Axis 66, on the other hand, represents the axis of rotation of cutter 30. For all practical purposes, axis 55 coincides with holes 40, 54 and the passageway 56 through which guide wire 60 is inserted. In any event, axis 66 is substantially parallel to axis 64 and the position of cutter 30 within housing 28 accordingly establishes a set off distance 68 which causes blade 50 to cyclically project through opening 42 during rotations of cutter 30. FIG. 4 shows the relative relationship between sheath 14 and torque tube 62 and gives a more complete appreciation of the protection afforded by sheath 14 for the rotatable torque tube 62.

While the particular athrectomy cutter as herein shown and disclosed in detail is fully capable of obtaining the objects and providing the advantages herein before stated, it is to be understood that it is merely illustrative of the presently
preferred embodiments of the invention and that no limitations are intended to the details of construction or design herein shown other than as defined in the appended claims.

I claim:

1. A device for removing obstructive tissue from a body vessel which comprises:
   a rotatable cutter having a blade; and
   a hollow cylindrical housing defining a cylindrical periphery, said housing being formed with a side opening, said housing supporting said cutter therein to cyclically project said blade from within said housing through said opening beyond said periphery during rotation of said cutter.

2. A device for removing obstructive tissue from a body vessel as recited in claim 1 further comprising a guide wire for supporting said cutter, said cutter being formed with a passageway for receiving said guide wire.

3. A device for removing obstructive tissue from a body vessel as recited in claim 2 further comprising a torque tube fixedly attached to said cutter for rotating said cutter, said torque tube being positioned for fluid communication with said passageway.

4. A device for removing obstructive tissue from a body vessel as recited in claim 3 further comprising a fixedly attached to said housing and positioned in surrounding relationship to said torque tube.

5. A device for removing obstructive tissue from a body vessel as recited in claim 4 further comprising suction means operatively connected with said torque tube for removing cuttings of obstructive tissue from said vessel through said passageway and said torque tube.

6. An apparatus for removing obstructive tissue from a body vessel which comprises:
   a housing having a periphery and defining a central longitudinal axis and having a side opening radially oriented relative to said longitudinal axis; and
   a cutter having a blade, said cutter rotatably mounted in said housing for rotation about an axis substantially parallel to and spaced from said central longitudinal axis to cyclically project said blade from said side opening beyond said periphery to cut the obstructive tissue.

7. A device for removing obstructive tissue from a body vessel as recited in claim 6 further comprising a guide wire for supporting said cutter, said cutter being formed with a passageway for receiving said guide wire.

8. A device for removing obstructive tissue from a body vessel as recited in claim 7 further comprising a torque tube fixedly attached to said cutter for rotating said cutter, said torque tube being positioned for fluid communication with said passageway.

9. A device for removing obstructive tissue from a body vessel as recited in claim 8 further comprising a sheath fixedly attached to said housing and positioned in surrounding relationship to said torque tube.

10. A device for removing obstructive tissue from a body vessel as recited in claim 9 further comprising suction means operatively connected with said torque tube for removing cuttings of obstructive tissue from said vessel through said passageway and said torque tube.

11. A method for removing obstructive tissue from the lumen of a body vessel which comprises the steps of:
    Inserting a guide wire into the lumen of a body vessel across the obstructive tissue;
    Advancing a cutting apparatus over said guide wire into contact with the obstructive tissue, said apparatus comprising a rotatable cutter having a blade, and a hollow cylindrical housing defining a periphery and having a side opening therethrough, said housing supporting said cutter therein to cyclically project said blade from within said housing through said opening beyond said periphery during rotation of said cutter to cut said obstructive tissue; and
    Rotating said cutter.

* * * * *